United States Patent [19]

Lee

[11] Patent Number: 4,868,193
[45] Date of Patent: Sep. 19, 1989

[54] STYRYL TETRAZOLES AND ANTI-ALLERGIC USE THEREOF

[75] Inventor: Thomas D. Y. Lee, Scarsdale, N.Y.

[73] Assignee: Rorer Pharmaceutical Corporation, Fort Washington, Pa.

[21] Appl. No.: 911,028

[22] Filed: Sep. 24, 1986

[51] Int. Cl.$^4$ .................... A61K 31/44; A61K 31/47; C07D 403/10; C07D 403/14
[52] U.S. Cl. .................... 514/314; 514/336; 514/381; 546/176; 546/276; 578/252
[58] Field of Search .................... 546/165, 176, 276; 514/314, 381, 336

[56] References Cited

U.S. PATENT DOCUMENTS

| 4,304,774 | 12/1981 | Katner | 574/90 X |
| 4,346,076 | 8/1982 | Katner | 544/27 |
| 4,404,214 | 9/1983 | Takeda et al. | 546/276 |

OTHER PUBLICATIONS

F. R. Benson, "The Tetrazoles" in Heterocyclic Compounds, vol. 8, edited by R. C. Elderfield, John Wiley & Sons, Inc., New York, 1967, pp. 11–19.
R. N. Butler, "Recent Advances in Tetrazole Chemistry" in Advances in Heterocyclic Chemistry, vol. 21, edited by A. R. Katritzky and A. J. Boulton, Academic Press, New York, 1977, pp. 254–355.

Primary Examiner—David B. Springer

[57] ABSTRACT

Compounds of the formula:

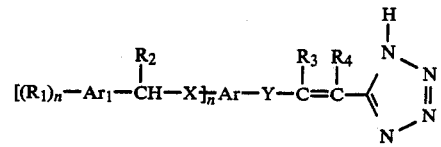

and salts thereof, wherein,
Ar$_1$ is phenyl, naphthyl or heterocyclic ring selected from the group consisting of quinolinyl, isoquinolinyl, pyridinyl, quinazolinyl, quinoxalinyl, benzimidazolyl, 1,2,3,4-tetrahydroquinolinyl or 1,2,3,4-tetrahydroquinoxalinyl;
R$_1$ is hydrogen, alkyl, carboxy, carbalkoxy, alkanoyl, formyl, nitrilo, amino, halo, CF$_3$, hydroxy, alkoxy, aralkoxy, aryloxy, nitro, sulfanyl, mercapto or alkylthio;
R$_2$ is hydrogen, alkyl or Ar$_1$,
n is 1 or 2
X is O, S, or NH—
Y is a bond, methylene or ethylene
R$_3$ and R$_4$ are independently hydrogen, alkyl or halo
Ar is phenyl, naphthyl, pyridyl or quinolinyl containing one or two substituents selected from the group consisting of hydrogen, alkoxy, aryloxy, hydroxy, hydroxyalkyl, alkyl, aryl, halo, CF$_3$, carboxy, carbalkoxy, lower acyl, nitrilo, amino, nitro, mercapto or alkylthio possess anti-inflammatory and anti-allergic activities.

13 Claims, No Drawings

STYRYL TETRAZOLES AND ANTI-ALLERGIC USE THEREOF

This invention relates to new chemical compounds possessing valuable pharmaceutical activity. More particularly, the invention relates to novel leukotriene antagonist compounds possessing antiinflammatory and antiallergic activities. Novel intermediates, used for preparing the active therapeutic agents, also possess valuable therapeutic properties, and are also within the scope of this invention.

SUMMARY OF THE INVENTION

The present invention is concerned with a compound of the formula:

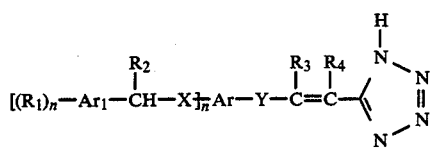

and salts thereof,
wherein,

Ar$_1$ is phenyl, naphthyl or heterocyclic ring selected from the group consisting of quinolinyl, isoquinolinyl, pyridinyl, quinazolinyl, quinoxalinyl, benzimidazolyl, 1,2,3,4-tetrahydroquinolinyl or 1,2,3,4-tetrahydroquinoxalinyl;

R$_1$ is hydrogen, alkyl, carboxy, carbalkoxy, alkanoyl, formyl, nitrilo, amino, halo, CF$_3$, hydroxy, alkoxy, aralkoxy, aryloxy, nitro, sulfamyl, mercapto or alkylthio;

R$_2$ is hydrogen, alkyl or Ar$_1$, n is 1 or 2

X is O, S, or NH—

Y is a bond, methylene or ethylene,

R$_3$ and R$_4$ are independently hydrogen, alkyl or halo,

Ar is phenyl, naphthyl, pyridyl or quinolinyl containing one or two substituents selected from the group consisting of alkoxy, aryloxy, hydroxy, hydroxyalkyl, alkyl, aryl, halo, CF$_3$, carboxy, carbalkoxy, lower acyl, nitrilo, amino, nitro, mercapto or alkylthio.

The alkyl groups in alkyl, alkoxy, carbalkoxy, alkanoyl, alkylthio, hydroxyalkyl contain from 1 to 6 carbon atoms and have either straight or branched structure. Such groups include methyl, ethyl, propyl, isopropyl, butyl, isobutyl, amyl, isoamyl, hexyl, and the like.

The halo groups contain F, Cl, Br, or I.

The aryl groups in aryl, aralkoxy are phenyl or naphthyl.

The new compounds of the present invention can be prepared by art-recognized procedures from known starting materials and intermediates.

An exemplary general synthetic route is as follows:

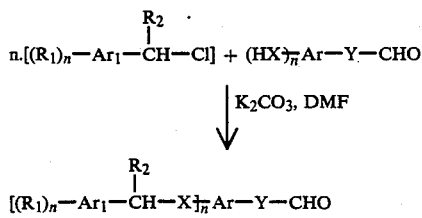

A hydroxyaraldehyde is alkylated with an appropriate aralkyl halide with heating in a high boiling solvent such as dimethylformamide (DMF) containing a base such as anhydrous potassium carbonate. The product is subjected to the Wittig reaction condition to yield an acrylonitrile. When hydrazoic acid (generated in situ by sodium azide and an acid) is added to the acrylonitrile, the tetrazole is obtained. (See, for example 1. F. R. Benson, "The Tetrazoles" in "Heterocyclic Compounds" Vol. 8, edited by R. C. Elderfield, John Wiley & Sons, Inc., New York, 1967, pp. 11–19.

2. R. N. Butler, "Recent Advances in Tetrazole Chemistry" in "Advances in Heterocyclic Chemistry", Vol. 21, edited by A. R. Katritzky and A. J. Boulton, Academic Press, New York 1977, pp. 354–355.)

Various preparation procedures are illustrated in the specific working examples which are included herein.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, maleic, acetic, malic, tartaric and the like which are pharmaceutically acceptable. Basic salts for pharmaceutical use are the Na, K, Ca and Mg salts.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, trouches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 10 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The therapeutic dosage will generally be from .10 to 750 milligrams per day and higher although it may be administered in several different dosage units. Tablets containing from 10 to 250 mg. of active agent are particularly useful.

DETAILED DESCRIPTION OF THE INVENTION

The following examples further illustrate the invention.

EXAMPLE 1A 3-(Quinolin-2-yl-methoxy)benzaldehyde

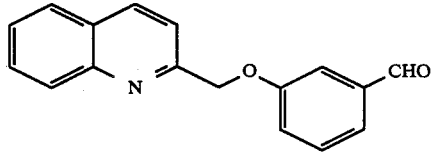

With stirring, a mixture of 3-hydroxybenzaldehyde (8.5 g), 2-chloromethylquinoline hydrochloride (17 g), and anhydrous potassium carbonate (100 g) in dimethylformamide (200 ml) was heated for 6 hours. After filtration, the solvent was removed with reduced pressure and the residue was partitioned between chloroform and water. The organic layer was dried and concentrated to an oil which upon cooling and treatment with hexane, gave the product as an off-white colored solid (16 g), m.p. 48°–53° C.

EXAMPLE 1B 3-(Quinolin-2-yl-methoxy)-cinnamylnitrile

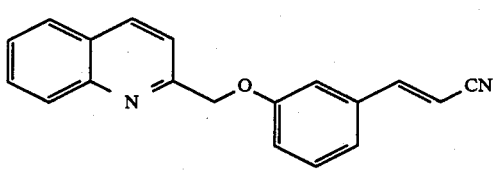

Sodium hydride (60% oil dispersion, 1.2 g) and diethyl cyanoosphonate (5 ml) were mixed and stirred in tetrahydrofuran (50 ml) for 5 minutes then added by a tetrahydrofuran solution of 1 A (7 g). The reaction mixture was stirred for additional 30 minutes and was poured to ice water thereafter to cause the precipitation of the crude product. It was filtered through a short silica gel dry column (chloroform as the eluant) to give the pure product as a white solid (4.8 g), m.p. 95°–98° C.

EXAMPLE 1C

5-[3-(Quinolin-2-yl-methoxy)styryl]-tetrazole hydrochloride

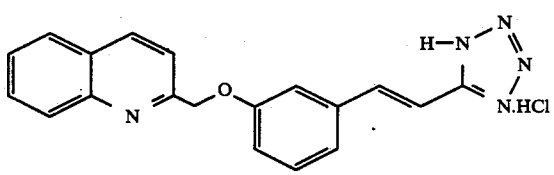

With stirring, a mixture of 1B (2.9 g), anhydrous alumiumchloride (1.4 g) and sodium azide (2.9 g) in tetrahydrofuran (30 ml) was refluxed for 18 hours. Hydrochloric acid (18% HCl, 15 ml) was added and thereafter the reaction mixture was poured to ice water. The precipitates were collected and then recrystalized from methanol-ethyl acetate to yield the pure product as an off-white solid (1.8 g), m.p. 201° C. (decomposed).

The free base can be obtained by treating 1C with one equivalent of sodium hydroxide solution followed by removal of sodium chloride and water.

EXAMPLE 2A 4-(Quinolin-2-yl-methoxy) benzaldehyde

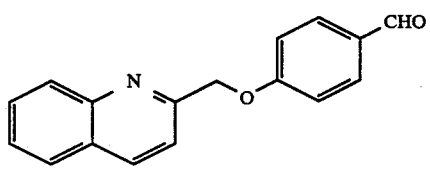

From a mixture of 4-hydroxybenzaldehyde (5 g), 2-chloromethylquinoline hydrochloride (10.8 g) and anhydrous potassium carbonate (80 g) in dimethylformamide (100 ml), a total of 6.6 grams of captioned product as an off-white colored solid, m.p. 69°–72° C., was prepared similarily as in Example 1A.

EXAMPLE 2B 4-(Quinolin-2-yl-methoxy)-cinnamylnitrile

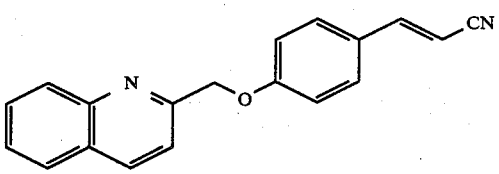

Prepared similarily as in Example 1B, 5.4 grams of product, m.p. 131°–134° C,, was obtained from 6.2 grams of 2A.

EXAMPLE 2C

5-[4-(Quinolin-2-yl-methoxy)styryl]-tetrazole hydrochloride

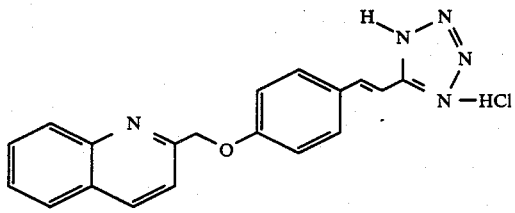

Prepared similarily as in Example 1C, from the product of 2B (2.9 g), anhydrous aluminum chloride (1.8 g) and sodium azide (2.9 g), a total of 2 grams of product as an off-white colored solid was obtained, m.p. 245° C. (decomposed).

The free base can be obtained by treating 2C with one equivalent of aqueous sodium hydroxide followed by removal of sodium chloride and water.

Following the procedures in the above examples, the following additional compounds can be obtained.

EXAMPLE 3

5-[2-(Quinolin-2-yl-methoxy)styryl]-tetrazole and its hydrochloride salt

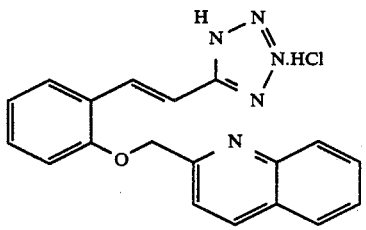

EXAMPLE 4

5-[4-Hydroxy-3-(quinolin-2-yl-methoxy)styryl]-tetrazole and its hydrochloride salt

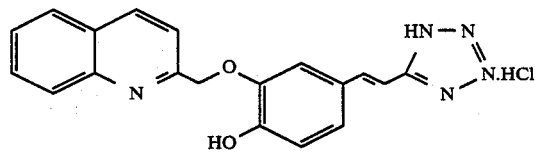

EXAMPLE 5

5-[3-Methyl-5-(quinolin-2-yl-methoxy)styryl]-tetrazole and its hydrochloride salt

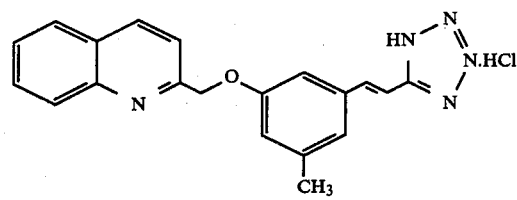

EXAMPLE 6

5-[3-(Quinoxalin-2-yl-methoxy)styryl]-tetrazole and its hydrochloride salt

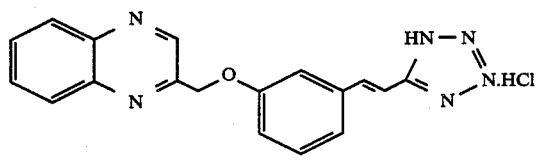

EXAMPLE 7

5-(3-Picolyloxy-styryl)-tetrazole and its hydrochloride salt

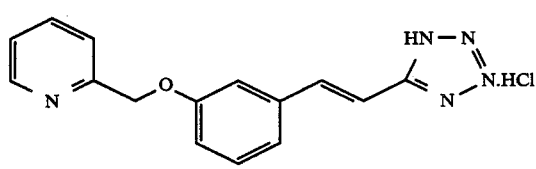

EXAMPLE 8

5-(3-Benzyloxy-styryl)-tetrazole and its hydrochloride salt

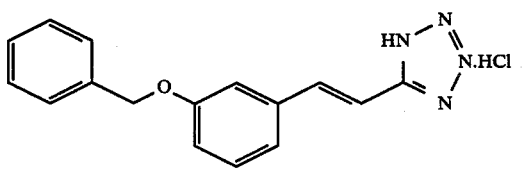

EXAMPLE 9

5-(3-Naphthal-2-yl-methoxy-styryl)tetrazole and its hydrochloride salt

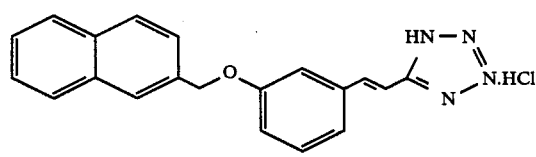

EXAMPLE 10

5-[3-(Isoquinolin-1-yl-methoxy)-styryl]-tetrazole and its hydrochloride salt

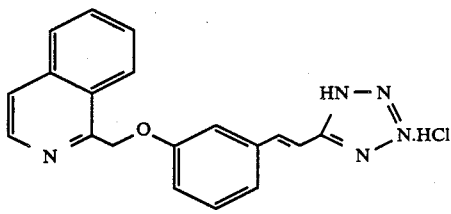

EXAMPLE 11

5-[3-(Benzimidazol-2-yl-methoxy)-styryl]-tetrazole and its hydrochloride salt

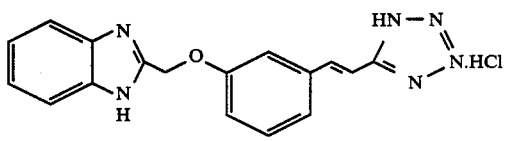

EXAMPLE 12

5-[3,4-Bis(quinolin-2-yl-methoxy)-styryl]-tetrazole and its hydrochloride salt

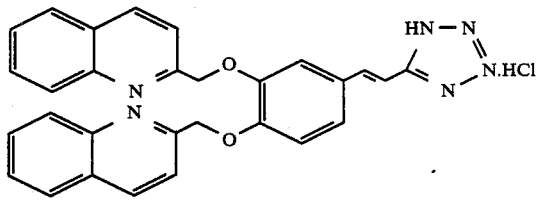

EXAMPLE 13

5-(3-Benzhydryloxy-styryl)-tetrazole and its hydrochloride salt

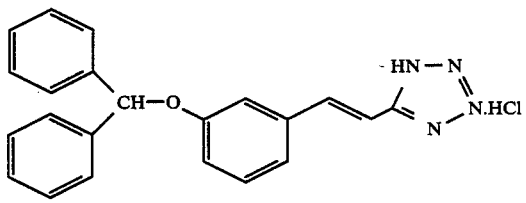

EXAMPLE 14

5-[3-((3-Quinolin-2-yl-methoxy)-phenyl)prophenyl]-tetrazole and its hydrochloride salt

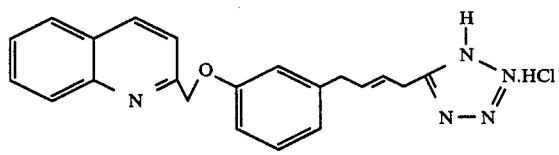

Compounds of the present invention are useful as prophylactic therapeutic agents in the treatment of various allergic diseases including asthma.

The following describe the test procedures used to evaluate anti-allergic/anti-asthmatic activity of the compounds.

Leukotrienes, the products of 5-lipoxygenase pathway of arachidonic acid metabolism (Samuelson et al. in : Adv. Prosta Thromboxane Research, Raven Press, Vol. 6, 1 (1980) are potent contractile agents with a variety of smooth muscle preparations (Drazen et al. Proc. Nat'l Acad. Sci., USA, 77, 4353 (1980)). Thus, it has been hypothesized that the leukotrienes contribute significantly to the pathophysiology of asthma (Fleish et al., J. Pharmacol. Exp. Thera., 221, 146 (1982)).

In Vitro Assay to Identify Leukotriene Antagonist Compounds

Preparation of Lung Strips

Peripheral strips of guinea pig lungs are prepared and hung in tissue baths according to the procedure described by Drazen et al. Male guinea pigs (Charles River, 250-400 g) are sacrificed by cervical dislocation and their lungs rapidly removed. The individual lobes are dissected free and rinsed in Assay Buffer which is continuously aerated with 95% oxygen—5% carbon dioxide. After the lobes are extensively rinsed, a strip of lung tissue, approximately 2 mm thick and 5-8 cm long, is cut off the sharpest and most peripheral portion of each lobe. The peripheral edge is cut almost completely around the outside of the lobe so that a U-shaped strip is obtained. These strips are rinsed in Assay Buffer and then connected with surgical silk thread to the support rods from the tissue baths. The rods are adjusted in the baths and the strips connected to the pressure transducers. The tissue baths are aerated with 95% oxygen—5% carbon dioxide and maintained at 37°. The tension on these strips is adjusted to 500 mg with "re-zeros" the pen deflection on the previously calibrated polygraph. Tissues are initially washed with fresh buffer every 5-10 minutes for about 30 minutes. Thereafter, tissues were washed with fresh assay buffer at least every 20 minutes.

Normalizing Muscle Contractions and Testing of Compounds

1. After the tissues have been repeatedly washed and allowed to equilibrate in the tissue bath, they are challenged with 1μM histamine. [Usually 10 μl of a 1 mM stock solution are added to the baths.] After maximum concentrations have been obtained, then tissues are washed and allowed to relax back to baseline tension. This histamine challenge procedure is repeated at least 1 or 2 more times to obtain a repeatable control response. Since there is a large variation in tissue responses to agonists, the averaged response to 1 μM histamine for each tissue is used to normalize all other challenges.

2. Responses of each tissue to a predetermined concentration

3. Usually test compounds are tested initially at 30 μM on resting tension of the tissues without any added agonist or antagonist to determine if the compound has any possible intrinsic activity. The tissues are then washed and the test compound is added again. Leukotriene (usually 0.4 units/ml) is added after the desired preincubation time and the muscle response is recorded. The experiment is repeated with several concentrations of the test compound to furnish a concentration response curve. From this curve the concentration responding to the 50% reduction of the muscle concentration is calculated as the $I_{50}$ value. Compounds with $I_{50}$ values less than 10 μM are considered potent antagonists of leukotrienes.

Leukotriene D4-Induced Wheal formation in the Guinea Pig

Leukotriene D4 (LTD4) increases vascular permeability in guinea pig skin. LTD4 antagonists are tested for oral activity in a model of LTD4-induced cutaneous wheal formation in the guinea pig. Male Hartley guinea pigs are given either vehicle (polyethylene glycol 400) or test compound by gauge one hour before intravenous injection of 1% Evans blue dye. Immediately after dye injection, 0.1 μg of LTD4 (in a volume of 0.1 ml) is injected intradermally at two separate dorsal sites. Thirty minutes later, the animals are sacrificed by carbon dioxide asphyxiation, the dorsal skins reflected, and glued wheal areas measured. Mean values±standard error for wheal areas in vehicle- and drug-treated groups are determined. Inhibition of wheal formation is calculated by comparison of drug-treated and control groups.

Compounds are screened via oral route and are considered very potent with $ED_{50}$ values less than 50 mg/kg.

Some typical test results are shown in Table I

TABLE I

| | In Vitro $I_{50}$ (μM) | | In Vivo LTD4 Wheal, $ED_{50}$ |
|---|---|---|---|
| Example 1C | 0.06 | (VS LTD4) | 22 mg/kg. p.o. |
| | 0.08 | (VS LTD4) | |
| | 0.15 | (VS LTC4) | |
| Example 1B | 0.65 | (VS LTD4) | |
| | 1.2 | (VS LTC4) | |
| Example 2C | 0.5 | (VS LTC4) | |

What is claimed is:

1. A compound of the formula

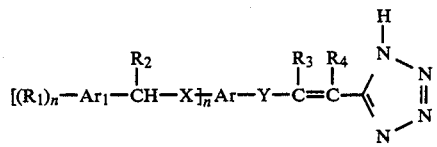

wherein:

AR1 is phenyl, quinolinyl, benzimidazoyl or 1,2,3,4-tetrahydroquinolinyl;

R1 is hydrogen, alkyl, alkanoyl, nitrilo, halo, CF3, alkoxy, phenylalkoxy, naphthylalkoxy, sulfamyl, or alkylthio;

R2 is hydrogen or alkyl;

n is 1 or 2;

X is O, S or NH;

Y is a carbon-carbon bond, methylene or ethylene;

R3 and R4 are independently hydrogen, alkyl or halo;

Ar is phenyl, naphthyl, pyridyl or quinolinyl, or phenyl, naphthyl, pyridyl or quinolinyl substituted with one or two substituents selected from the group consisting of alkyl, hydroxy, phenoxy, naphthlloxy, halo or alkylthio; and wherein:

the alkyl groups of alkyl, alkoxy, carbalkoxy, alkanoyl and alkylthio are straight or branched chain and contain from 1 to about 6 carbon atoms; and provided that when Ar₁ is phenyl, Ar is quinolinyl; and pharmaceutically acceptable salts thereof.

2. A compound according to claim 1 wherein said alkyl group is methyl, ethyl, propyl, isopropyl, butyl, isobutyl, amyl, isoamyl or hexyl.

3. A pharmaceutical composition for the treatment of allergic conditions comprising an effective amount of a compound of the formula

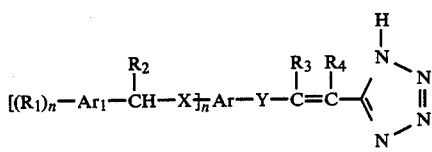

wherein:
Ar₁ is phenyl, quinolinyl, benzimidazoyl or 1,2,3,4-tetrahydroquinolinyl;
R₁ is hydrogen, alkyl, alkanoyl, nitrilo, halo, CF₃, alkoxy, phenylalkoxy, naphthylalkoxy, sulfamyl, or alkylthio;
R₂ is hydrogen or alkyl;
n is 1 or 2;
X is O, S or NH;
Y is a carbon-carbon bond, methylene or ethylene;
R₃ and R₄ are independently hydrogen, alkyl or halo;
Ar is phenyl, naphthyl, pyridyl or quinolinyl, or phenyl, naphthyl, pyridyl or quinolinyl substituted with one or two substituents selected from the group consisting of alkyl, hydroxy, phenoxy, naphthyloxy, halo or alkylthio; and wherein:
the alkyl groups of alkyl, alkoxy, carbalkoxy, alkanoyl and alkylthio are straight or branched chain and contain from 1 to about 6 carbon atoms; and
provided that when Ar₁ is phenyl, Ar is quinolinyl; and pharmaceutically acceptable salts thereof; in admixture with a pharmaceutically acceptable carrier.

4. A pharmaceutical composition according to claim 3 wherein said alkyl group is methyl, ethyl, propyl, isopropyl, butyl, isobutyl, amyl, isoamyl or hexyl.

5. A method a treating allergic conditions in a mammal comprising administering to said mammal an effective amount of a composition to relieve such allergic condition, said composition comprising an effective anti-allergic amount of a compound of the formula

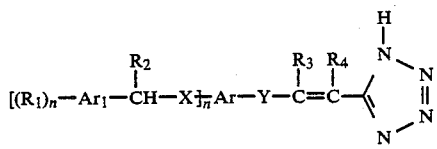

wherein:
Ar₁ is phenyl, quinolinyl, benzimidazoyl or 1,2,3,4-tetrahydroquinolinyl;
R₁ is hydrogen, alkyl, alkanoyl, nitrilo, halo, CF₃, alkoxy, phenylalkoxy, naphthylalkoxy, sulfamyl, or alkylthio;
R₂ is hydrogen or alkyl;
n is 1 or 2;
X is O, S or NH;
Y is a carbon-carbon bond, methylene or ethylene;
R₃ and R₄ are independently hydrogen, alkyl or halo;
Ar is phenyl, naphthyl, pyridyl or quinolinyl, or phenyl, naphthyl, pyridyl or quinolinyl substituted with one or two substituents selected from the group consisting of alkyl, hydroxy, phenoxy, naphthyloxy, halo or alkylthio; and wherein:
the alkyl groups of alkyl, alkoxy, carbalkoxy, alkanoyl and alkylthio are straight or branched chain and contain from 1 to about 6 carbon atoms; and
provided that when Ar₁ is phenyl, Ar is quinolinyl; and pharmaceutically acceptable salts thereof; in admixture with a pharmaceutically acceptable carrier.

6. A method according to claim 5, wherein said alkyl group is methyl, ethyl, propyl, isopropyl, butyl, isobutyl, amyl, isoamyl or hexyl.

7. 5-[3-(Quinolin-2-yl-methoxy)styryl]-tetrazole hydrochloride.

8. 5-[4-(Quinolin-2-yl-methoxy)styryl]-tetrazole hydrochloride.

9. 5-[2-(Quinolin-2-yl-methoxy)styryl]-tetrazole hydrochloride salt.

10. 5-[3-methyl-5-(quinolin-2-yl)-methoxy)styryl]-tetrazole and its hydrochloride salt.

11. 5-[4-Hydroxy-3-(quinolin-2-yl-methoxy)styryl]-tetrazole and its hydrochloride salt.

12. 5-[3,4-Bis(quinolin-2-yl-methoxy)-styryl]-tetrazole and its hydrochloride salt.

13. 5-[3-{(3-Quinolin-2-yl-methoxy)phenyl} propenyl]-tetrazole and its hydrochloride salt.

* * * * *